United States Patent [19]

Kundu

[11] Patent Number: 5,958,716
[45] Date of Patent: Sep. 28, 1999

[54] BLOOD FACTOR ASSAY

[75] Inventor: Sourav K. Kundu, Cooper City, Fla.

[73] Assignee: Dade Behring Inc., Deerfield, Ill.

[21] Appl. No.: 08/656,973

[22] Filed: Jun. 6, 1996

[51] Int. Cl.$^6$ ........................................ C12Q 1/56
[52] U.S. Cl. .................. 435/13; 435/2; 435/372; 435/383; 436/518; 436/536; 530/380; 530/381; 530/383
[58] Field of Search ..................... 436/518, 536; 435/2, 372, 383, 13; 530/380, 381, 383

[56] References Cited

U.S. PATENT DOCUMENTS

| | | |
|---|---|---|
| 2,616,796 | 11/1952 | Schilling et al. . |
| 3,219,421 | 11/1965 | Schwartz, Jr. et al. . |
| 3,267,362 | 8/1966 | Page . |
| 3,267,364 | 8/1966 | Page et al. . |
| 3,268,804 | 8/1966 | Young . |
| 3,539,300 | 11/1970 | Stone . |
| 3,605,010 | 9/1971 | Folus . |
| 3,694,161 | 9/1972 | Kleszynski et al. . |
| 3,914,985 | 10/1975 | von Behrens . |
| 3,918,908 | 11/1975 | Moyer et al. . |
| 4,281,061 | 7/1981 | Zuk et al. ............................. 435/188 |
| 4,451,568 | 5/1984 | Schneider et al. . |
| 4,458,678 | 7/1984 | Yannas et al. . |
| 4,533,519 | 8/1985 | Baugh et al. . |
| 4,534,939 | 8/1985 | Smith et al. . |
| 4,599,219 | 7/1986 | Cooper et al. . |
| 4,604,894 | 8/1986 | Kratzer et al. . |
| 4,663,127 | 5/1987 | Jackson et al. . |
| 4,752,449 | 6/1988 | Jackson et al. . |
| 4,777,141 | 10/1988 | Calzi et al. . |
| 4,780,418 | 10/1988 | Kratzer . |
| 4,784,944 | 11/1988 | Kolde . |
| 4,788,139 | 11/1988 | Ryan . |
| 4,812,293 | 3/1989 | McLaurin et al. . |
| 4,865,813 | 9/1989 | Leon . |
| 4,983,514 | 1/1991 | Weithmann et al. . |
| 5,047,211 | 9/1991 | Sloane, Jr. et al. . |
| 5,051,239 | 9/1991 | von der Goltz . |
| 5,089,422 | 2/1992 | Brubaker . |
| 5,091,304 | 2/1992 | La Duca et al. . |
| 5,093,237 | 3/1992 | Enomoto . |
| 5,111,946 | 5/1992 | Glanz . |
| 5,128,104 | 7/1992 | Murphy et al. . |
| 5,139,944 | 8/1992 | Sawyer et al. . |
| 5,140,161 | 8/1992 | Hillman et al. . |
| 5,174,961 | 12/1992 | Smith . |
| 5,187,102 | 2/1993 | Stocker et al. . |
| 5,196,403 | 3/1993 | Maraganore et al. . |
| 5,197,017 | 3/1993 | Carroll et al. . |
| 5,221,614 | 6/1993 | Enomoto . |
| 5,223,227 | 6/1993 | Zuckerman . |
| 5,246,666 | 9/1993 | Vogler et al. . |
| 5,246,715 | 9/1993 | Orevi et al. . |
| 5,275,953 | 1/1994 | Bull . |
| 5,281,661 | 1/1994 | Linnau et al. . |
| 5,314,826 | 5/1994 | Baugh . |
| 5,316,730 | 5/1994 | Blake et al. . |
| 5,339,830 | 8/1994 | Blake, III . |
| 5,352,413 | 10/1994 | Kratzer et al. . |
| 5,366,869 | 11/1994 | Goldstein et al. ....................... 435/13 |
| 5,427,913 | 6/1995 | Shaw et al. ............................ 435/7.21 |
| 5,460,779 | 10/1995 | Kratzer et al. . |
| 5,569,590 | 10/1996 | Speck ..................................... 435/13 |

FOREIGN PATENT DOCUMENTS

| | | |
|---|---|---|
| 0 186 476 A2 | 7/1986 | European Pat. Off. . |
| 4209871 | 12/1992 | Germany . |
| 0 774 261 A2 | 5/1997 | Germany . |
| 2 096 329 | 10/1982 | United Kingdom . |
| 96/00898 | 1/1996 | WIPO . |

OTHER PUBLICATIONS

"PFA Reagents", Dade.
"Thromboplastin–C; Dried Rabbit Brain Thromboplastin with Calcium For use in prothrombin time (PT) determinations and prothrombin time based assays", Baxter.
Activated Cephaloplastin Reagent—Liquid Rabbit Brain Cephalin with Plasma Activator, Baxter.
Product inclosure: Repllplate—American Diagnostica Inc., 1991.
Product inclosure—Bio/Data Corporation, 1981.
Product inclosure: Purified Human vWF—American Diagnostica Inc., 1993.
"Platelet Function Analyzer PFA–100", Baxter.
Colman et al., *Hemostasis and Thrombosis*, Basic Principles and Clinical Practice, pp. 143–149.
Allain et al., *J. Lab. Clin. Med*, 1975, "Platelets fixed with paraformaldehyde: a new reagent for assay of von Willebrand factor and platelet aggregating factor", pp.318–328.
Miller et al., *J. Clin. Invest.*, The American Society for Clinical Investigation, Inc., vol. 72, 1983, pp. 1532–1542.
Kratzer et al., *Haemostasis,* 15:357–362 (1985), "Simulation of Primary Haemostasis In Vitro".

(List continued on next page.)

*Primary Examiner*—James C. Housel
*Assistant Examiner*—Jennifer Graser
*Attorney, Agent, or Firm*—Cara Z Lowen; Lois K Ruszala

[57] ABSTRACT

The present invention provides a method for indicating von Willebrand factor deficiency in a blood sample or platelet-rich plasma sample which exhibits abnormal platelet function comprising (a) adding a von Willebrand factor preparation to the sample, and (b) testing the sample for platelet function. In this method, the von Willebrand factor preparation restores normal platelet function and indicates that the sample initially lacked the von Willebrand factor. The von Willebrand factor preparation comprises purified von Willebrand factor. The invention also discloses a method which further comprises separating the blood sample into a plasma layer and cellular component layer and removing the plasma layer, prior to the step of adding a von Willebrand factor preparation to the sample. In this embodiment the von Willebrand factor preparation comprises platelet-poor plasma containing a normal level of von Willebrand factor. The invention further provides a kit for indicating von Willebrand factor deficiency in a blood sample which exhibits abnormal platelet function comprising a von Willebrand factor preparation, wherein the preparation is added to the sample and restores normal platelet function, indicating that the sample initially lacked the von Willebrand factor.

16 Claims, 4 Drawing Sheets

OTHER PUBLICATIONS

Kratzer et al., *Haemostasis,* 15:363–370 (1985), "Detection of Abnormal Platelet Functions With an In Vitro Model of Primary Haemostasis".

Weiss et al., *Blood,* vol. 68, No. 1, 1986, pp. 149–156.

Maurin, *The International Journal Of Artificial Organs,* vol. 11, No. 4, (1988), "The In vitro Bleeding Time While Using A Stable Prostacyclin Analogue During Hemodialysis".

Tsujinaka et al., *Japanese Journal Of Surgenry,* vol. 18, No. 4, pp. 430–437, (1988), "Clinical Application of a New in vitro Bleeding Time Device on Surgical Patients".

Kretschmer et al., *Blut,* 59:188 (1989), "In Vitro Bleeding Test—A Sensitive Method For The Detection Of Platelet Function Impairment And A Potential Test For The Control Of Low–Dose Aspirin Efficacy".

Kretschmer et al., *Thrombosis Research,* 56:593–602 (1989), "In Vitro Bleeding Test—A Simple Method For The Detection Of Aspirin Effects On Platelet Function".

Dietrich et al., *Infusionstherapie,* 17:214–216 (1990), "Primary Hemostatis in Hemodilution—2) Infusion Solutions".

Alshameeri et al., *Thromb. Haemost 1993,* 69:1146, "Evaluation Of An In Vitro Bleeding Time Device, Thrombostat 4000".

Kretschmer et al., *Transfus. Sci.,* 14:27–34 (1993), "Determination of Bleeding Risk in Thrombocytopenic Patients Receiving Platelet Substitution".

Dietrich et al., *Lab. Med.,* 17:317–323, (1993), "The In Vitro Bleeding Test Standardization Of The Methodical Procedure".

Eriksson et al., *Eur. J. Haematol.,* 51:152–155 (1993), "Functional Capacity Of Transfused Platelets Estimated By The Thrombostat 4000/2".

Kundu et al., *Seminar in Thrombosis and Hemostasis,* vol. 21, Suppl. 2, 1995, "Description of an In Vitro Platelet Function Analyzer–PFA–100", pp. 106–112.

Mammen et al., *Seminar in Thrombosis and Hemostasis,* vol. 21, Suppl. 2, 1995, "Preliminary Data from a Field Trial of the PFA–100 System", pp. 113–121.

BLOOD FACTOR ASSAY

BACKGROUND OF THE INVENTION

Hemostasis or stoppage of bleeding involves the interplay of two biochemical pathways (the extrinsic and intrinsic pathways) which are controlled by various protein factors and formed elements, e.g., platelets. The processes by which blood coagulates as it is presently understood involve a multi-step cascade of activations of the protein factors that culminate in fibrin formation. Interference with any one step in these intricate processes hinders proper blood clotting and can result in significant bleeding.

Various tests have been developed to test the individual steps of the cascade involved in blood clotting in order to determine whether the blood of a patient can properly clot or whether there is clotting disorder in which there is a deficiency of one or more of the factors necessary for proper clotting.

There are a number of bleeding disorders which result in abnormal blot clotting including von Willebrand disease, factor VIII deficiency (hemophilia), afirinogenimia, platelet dysfunction (e.g., Bernard-Soutier Syndrome, Glanzman's Thrombasthemia, and storage pool disease). Individuals afflicted with these disorders suffer a potential risk of severe bleeding. Methods to determine the deficiency which is the cause of the disorder are desirable for immediate clinical and therapeutic intervention.

It is well known that the condition of the platelets or the platelet function of blood is one indication of the ability of blood to properly clot. vWf deficiency is one of the more common types of platelet dysfunction that occurs in approximately 1% of the population. vWf is a large multimeric glycoprotein which has an important role in the adhesion of platelets to the subendothelium following blood vessel damage. The interaction of vWf is essential for normal hemostasis.

The more common types of von Willebrand disease (vWD) include: a lack of the normal amount of vWf (mild or severe deficiency), and type IIA and type IIB vWD (which result from the deficiency of functional vWf proteins). Type IIB vWD is characterized by the absence of the high molecular weight multimers of vWf in the plasma. Type IIA vWD is characterized by the absence of both the intermediate and the high molecular weight multimers of vWf. Type IIA is further characterized by a decreased affinity of vWf for the platelet receptor glycoprotein Ib (GPIb), whereas in type IIB vWD, the vWf has an increased affinity for GPIB. See Ribba, et al., *J. Biol. Chem.*, 267 (32):23209–15 (1992). Type IIA is the most common type II variant of vWD. Ruggeri, et al., *J. Clin. Invest.*, 65:1318 (1980).

The primary existing test in use for testing platelet function or primary hemostasis on patients is known as the "bleeding time test". The bleeding time test which has existed for several decades involves making an incision in the forearm of the patient with a blood pressure cuff inflated to 40 mm Hg. Filter-paper is used to absorb the blood from the incision and to determine the amount of time for bleeding to stop. Bleeding usually stops within 10 minutes. The clinical utility of the test is limited by variability associated with the depth of the incision, the pressure applied, fluctuations in blood pressure of agitated patients, the method of absorbing blood with the filter paper, the direction of the cuts, among others. The variables are difficult to control and lead to problems with standardization and interpretation. Accordingly, a test for platelet function which does not involve making an incision and which is also more accurate was developed.

U.S. Pat. Nos. 4,604,894; 4,780,418; and 5,051,239 disclose an assay system which can be used to perform an in vitro test on blood for platelet function, the results of which can be correlated to the in vivo bleeding time test described above, thereby eliminating involvement of the patient. The Thrombostat™ 4000 (Dade International, Inc.), in current use, is one such system.

Platelet function is evaluated in the Thrombostat™ 4000 by aspirating anticoagulated whole blood samples at a constant negative pressure through a small aperture positioned at the center of a separating wall which may be non-porous or porous. In systems wherein the separating wall is porous, it is wetted prior to the start of the assay with an activator that activates coagulation of blood platelets. A platelet plug forms at the aperture and the time required for the cessation of blood flow to occur is determined. The time required to obtain full occlusion of the aperture is termed "in vitro bleeding time". This time is then correlated to platelet function assessed by conventional platelet aggregometry, or in vivo bleeding time.

The aforementioned in vitro assay systems which enable the determination of platelet dysfunction, however, do not discriminate between the various deficiencies which can cause the abnormal clotting. A physician utilizing such a system therefore does not know whether the dysfunction is caused by a vWf deficiency, or a less common platelet function disorder, thereby making treatment more difficult.

The current techniques for indicating vWf deficiency include: quantitative assays, e.g., immunologic detection of vWf; platelet aggregation assays, e.g. ristocetin cofactor assay with fixed platelets; and optical measurement of ristocetin-induced platelet aggregation. See *Hemostasis and Thrombosis; Basic Principles and Clinical Practice,* 3rd ed., eds. Colman, R. W., et al., J.B. Lippincott Co. (1994). These are static assays, in that they do not simulate in vivo clotting conditions. These assays are also performed on plasma, rather than whole blood, which adds steps and time to the performance of the assay. In some assays, platelet-rich plasma is used, other assays use platelet-poor plasma with added platelets, while still others use washed, gel-filtered or fixed platelets. See eg., Miller, et al., *J. Clin. Invest.,* 72:1532–1542 (1983); Allain, et al., *J. Lab. Clin. Med., Feb.*:318–328 (1975).

It would be useful to have a von Willebrand factor deficiency assay which tests clotting on samples of whole blood under conditions that are representative of in vivo conditions. The currently known techniques, described above, are complicated, time consuming and available only in specialized clinical laboratories. Results are usually delayed, sometimes requiring half a day under the best of circumstances, and more typically requiring 1 to 2 days in the usual clinical setting. This delay in obtaining the results leads to a delay in identification of the cause of the bleeding disorder and a delay in treatment. Delayed results are unacceptable in certain situations, such as in emergency surgical procedures.

It is therefore desirable to have a method for rapid indication of vWf deficiency.

SUMMARY OF THE INVENTION

Figure 1:
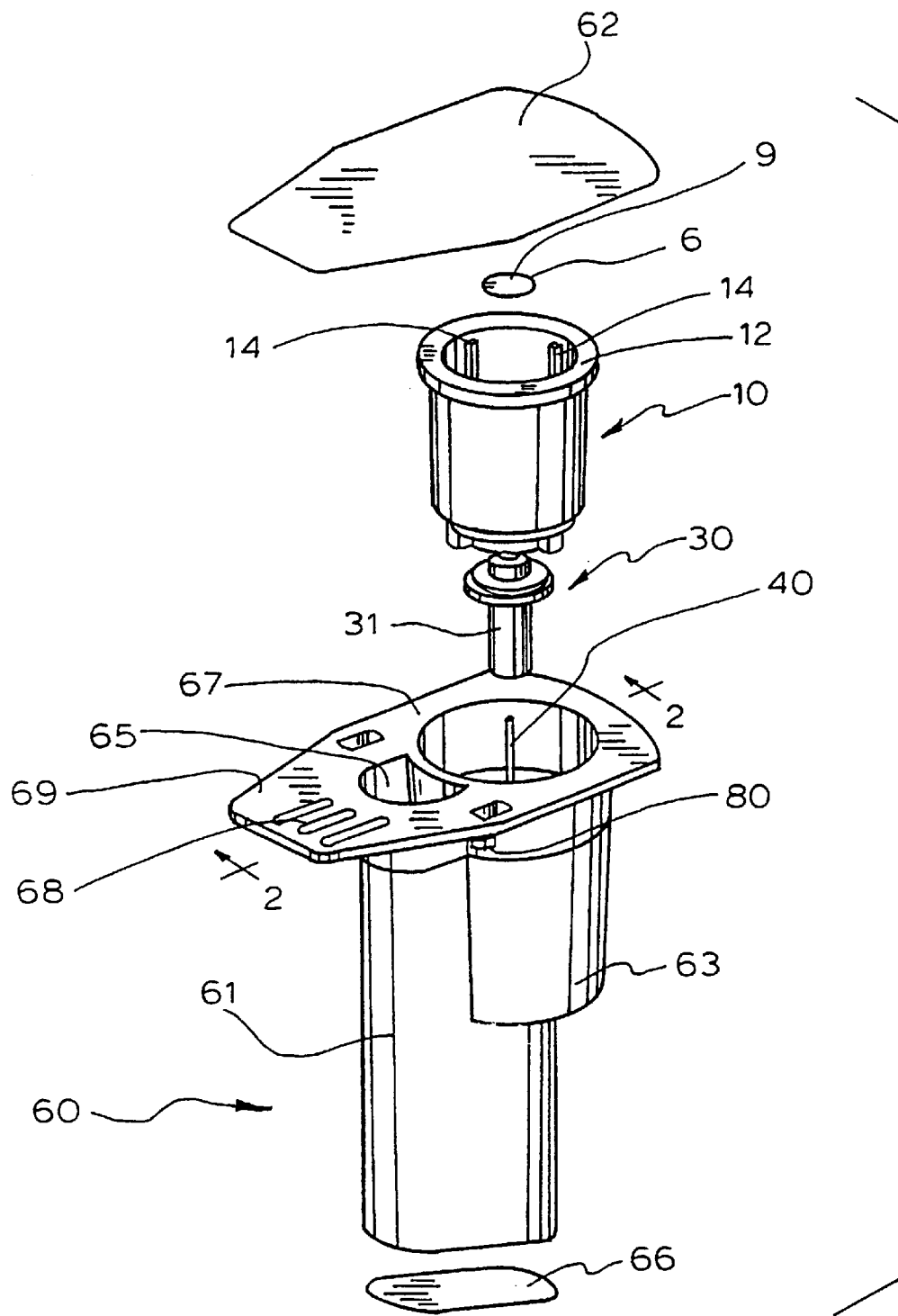
FIG. 1 shows a test cartridge for use in one preferred embodiment of the present method.

The invention provides a method for rapid indication of vWf deficient patients for immediate clinical and therapeutic intervention. More specifically, the method of the present invention indicates vWf deficiency where the deficiency is, e.g., an abnormal amount of, or substantial absence of the vWf protein, or a lack of a functional vWf protein. The lack of a functional protein is due to an abnormality in the molecular composition of the vWf protein (e.g., lack of high and intermediate molecular weight multimers, which causes type IIA vWD).

The present invention provides a method for indicating vWf deficiency in a blood sample or platelet-rich plasma sample that exhibits abnormal platelet function in a test for platelet function wherein the method comprises adding a vWf preparation to the sample, and testing the sample for platelet function wherein the vWf preparation restores normal platelet function and indicates that the sample initially had a vWf deficiency.

In one preferred embodiment of this method, the vWf preparation comprises purified vWf. Preferably the purified factor is added in an amount to obtain an activity comparable to the activity of vWf in normal blood. This amount will vary depending upon the specific activity of the purified vWf preparation. Preferably the purified vWf is added in an amount within the range of from about 3 μg/mL to about 100 μg/mL, more preferably from about 10 μg/mL to about 80 μg/mL, most preferably 30 μg/mL to 50 μg/mL. When using commercially available preparations of purified vWf (e.g., American Diagnostica), it is preferred that the factor be added at a concentration higher than the vWf concentration in normal plasma which is approximately 3–12 μg/mL.

In another embodiment of the present invention, the method comprises the steps of separating a whole blood sample into a plasma layer and a cellular component layer, removing the plasma layer, adding a vWf preparation to the cellular component layer of the sample, and testing the sample for platelet function wherein the normal platelet function indicates that the sample initially had a vWf deficiency. In such an embodiment, the vWf preparation comprises platelet-poor plasma containing a normal level of vWf.

In one preferred embodiment of the present invention is provided a method for determining vWf deficiency in a blood sample that exhibits platelet dysfunction wherein the testing of platelet dysfunction comprises measuring closure times in a device for testing hemostatic function of blood.

In a preferred embodiment the results are obtained within approximately 30 minutes and preferably in about 10 minutes.

The method of the present invention is useful for indicating vWf deficiency in a patient, wherein the vWf deficiency comprises an abnormal amount of the vWf protein, substantial absence of the vWf protein, or a lack of a functional vWf protein. The method is especially useful in indicating vWf deficiency where the lack of a functional vWf protein is due to an abnormality in the molecular composition of the vWf protein. The method is preferably useful where the abnormality causes Type IIA von Willebrand disease. A substantial absence of vWf protein occurs when the sample contains an amount of vWf significantly lower than the amount necessary for normal hemostasis, such as in Type III vWD. Examples of vWf deficiency, wherein the vWf deficiency is due to an abnormal amount of the vWf protein comprises Type I vWD.

The invention further provides a kit for indicating von Willebrand factor deficiency in a blood sample or platelet-rich plasma sample which exhibits abnormal platelet function. The kit comprises a von Willebrand factor preparation, which when added to the sample restores normal platelet function and indicates that the sample initially lacked the von Willebrand factor. In one kit embodiment, the von Willebrand factor preparation comprises purified von Willebrand factor. Preferably, the purified von Willebrand factor is added in amount to obtain an activity comparable to the activity of von Willebrand factor in normal blood. In another kit embodiment, the von Willebrand factor preparation comprises platelet-poor plasma containing a normal level of von Willebrand factor. Preferably, the platelet-poor plasma for use in such kits comprises fresh pooled platelet-poor plasma containing normal levels of von Willebrand factor, or freshly-thawed frozen normal pooled platelet-poor plasma, containing normal levels of vWf.

DETAILED DESCRIPTION OF THE INVENTION

The present invention provides for a rapid method of indicating vWf deficiency in whole blood samples which exhibit platelet dysfunction, enabling timely treatment of the resultant bleeding disorder.

The determination of platelet dysfunction can be achieved by any method known in the art, including that described by Brubaker, U.S. Pat. No. 5,089,422 or von der Goltz, U.S. Pat. No. 5,051,239. Other methods such as conventional aggregometry can also be used.

Preferably, the initial determination of platelet dysfunction in blood samples and the subsequent identification of vWf deficiency in those blood samples according to the methods of the present invention is accomplished using the PFA-100™ (Platelet Function Analyzer) test, described in copending applications Ser. Nos.: 08/269,184 and 08/269,185, incorporated herein by reference. The methods of the present invention will be illustrated using this particular test device. However, it is to be understood that the present invention is not limited to this test device.

One preferred embodiment described in copending application Ser. No.: 08/269,184, is a test cartridge specifically adapted for use in an assay for testing a coagulation function of blood such as the measurement of platelet function, including but not limited to automated versions of those assays described in U.S. Pat. Nos. 4,604,894, 4,780,418, and 5,051,239. This test cartridge comprises: a housing, which comprises a holding chamber for receiving a sample of the blood to be tested and a test chamber, wherein the holding chamber and test chamber are separated by a pierceable member; a partition member disposed in the test chamber, the partition member having an opening therethrough and comprising at least one reagent which activates at least one pathway of the coagulation of blood; a transfer member movably mounted in the test chamber so that it can be moved towards and pierce the pierceable member; and a receiving chamber disposed in the test chamber between the partition member and the transfer member for receiving blood from the transfer member. In use, blood is disposed by a user in the holding chamber and the test cartridge is placed in an instrument for incubation. After incubation, the transfer member is moved towards and pierces the pierceable member to contact the blood and a vacuum is created in the test chamber, blood moves through the transfer member into the receiving chamber and through the opening in the partition member.

In one preferred embodiment, described in co-pending application U.S. Ser. No. 08/621,821, the pierceable member has a cut therein. The cut is configured so that the transfer member moves easily through the cut. However, the cut is made so that the separating function of the pierceable member is not impaired.

Figure 2:
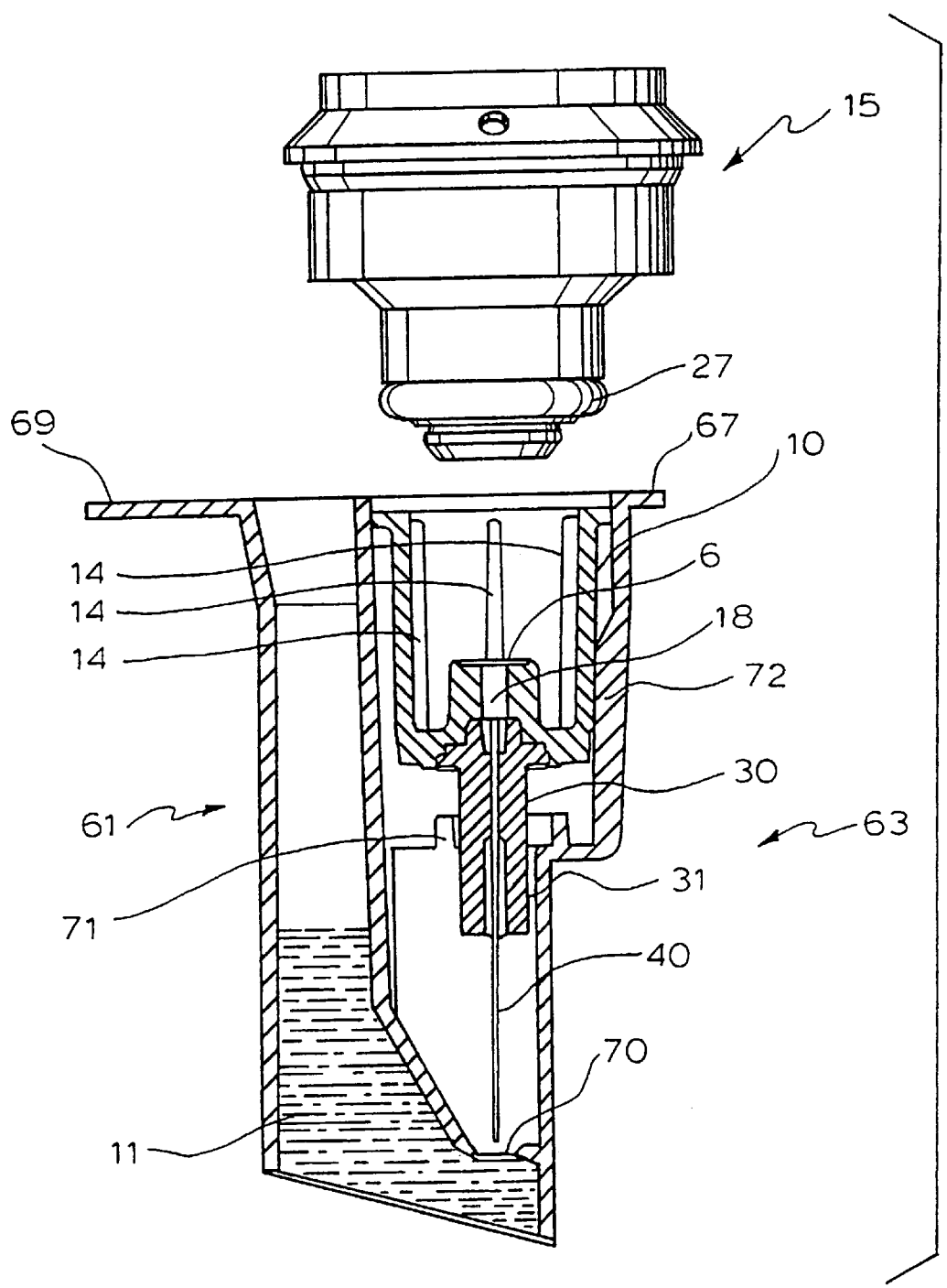
FIG. 2 is a cross section taken along line 2—2 of FIG. 1 wherein the device shown in FIG. 1 is in assembled form and further shows a portion of an instrument for use with the devices of the present invention.
Figure 3:
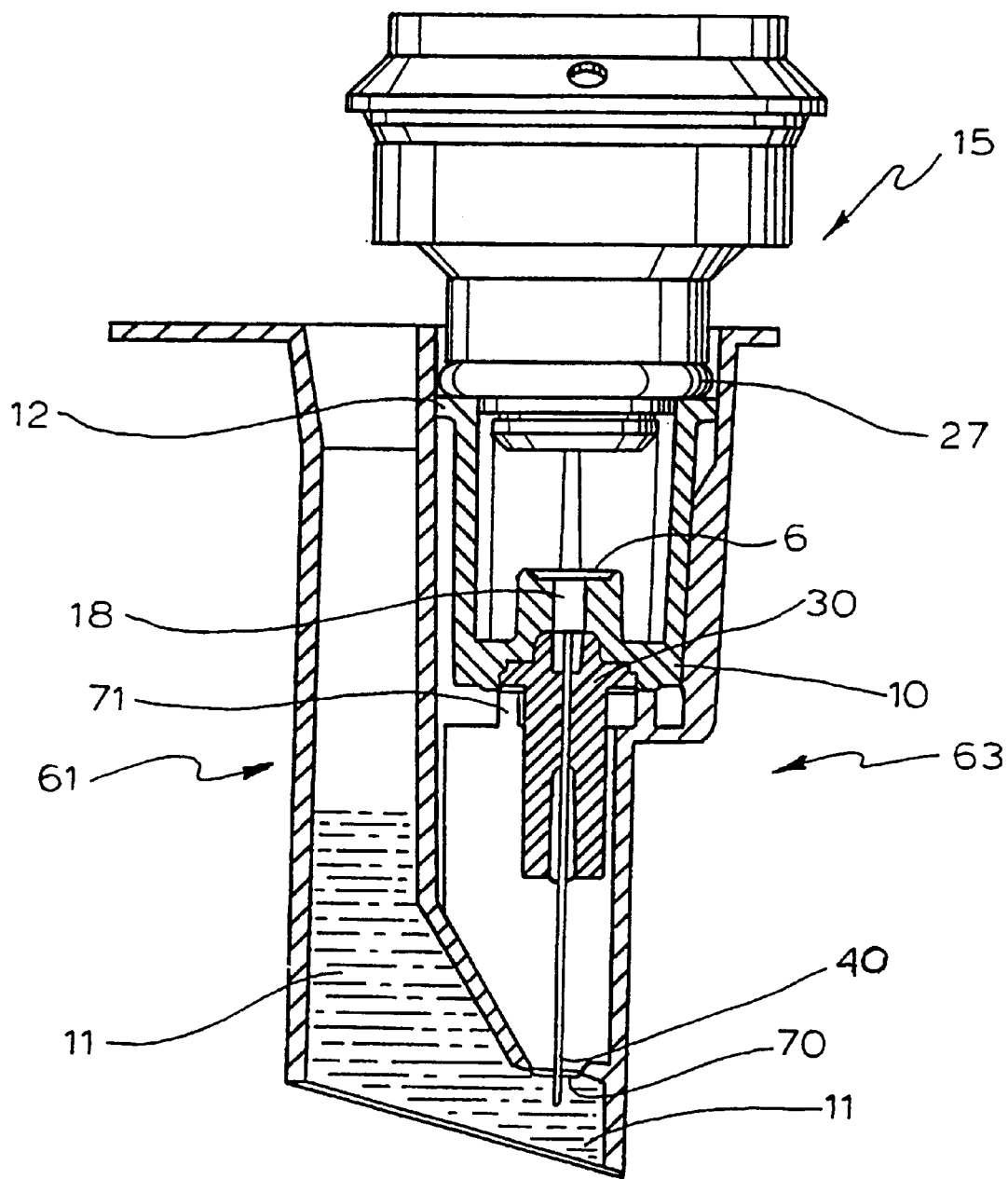
FIG. 3 is similar to FIG. 2, but shows the portion of the instrument having contacted and moved a component of the device shown in FIG. 2 from a first into a second position.
Figure 4:
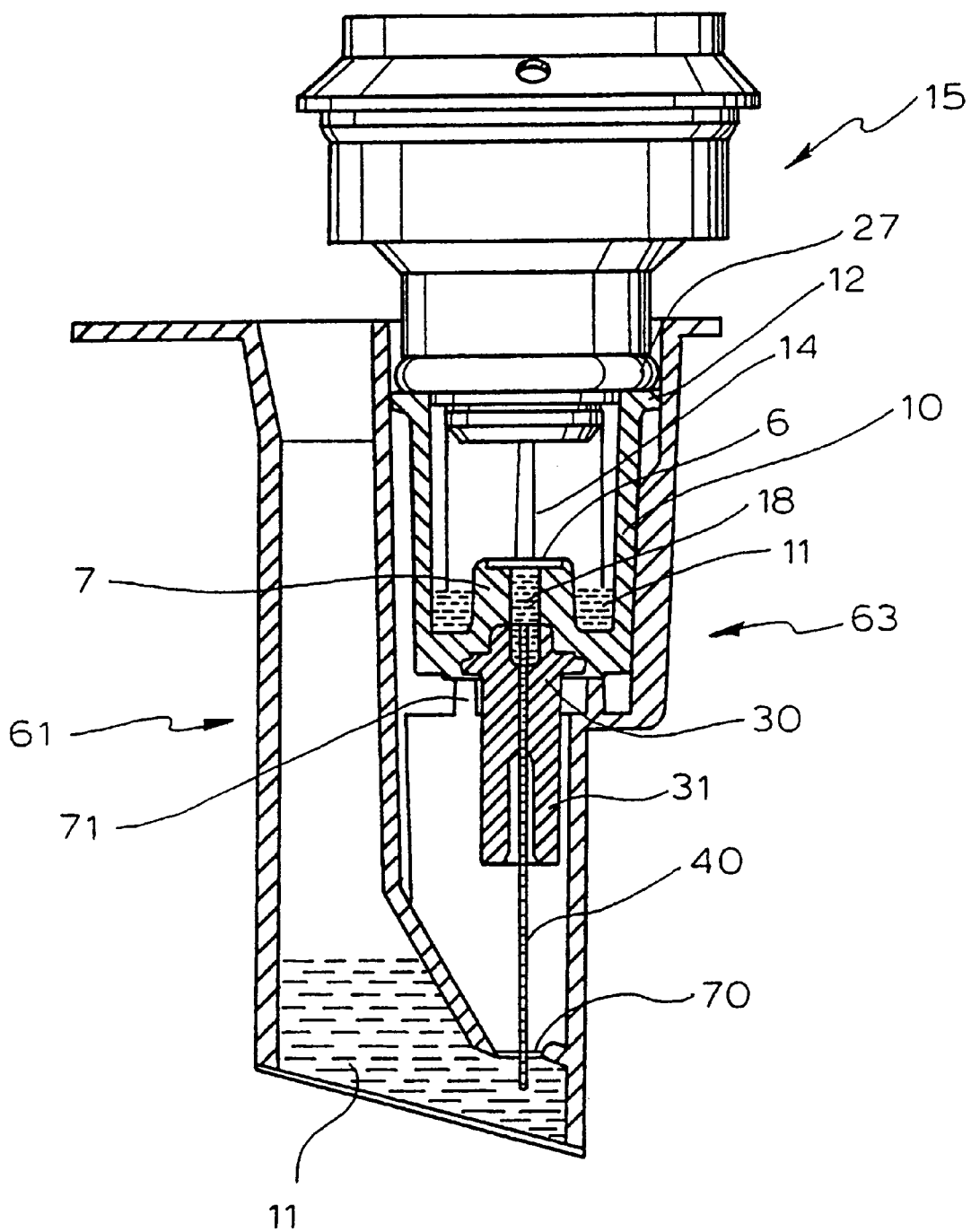
FIG. 4 is similar to FIG. 3 but shows sample having moved through the device.

FIG. 1 shows an isometric, exploded view of one such preferred device. A cross section of the device along line 2—2 of FIG. 1 in assembled form and containing sample 11 is shown in FIGS. 2, 3 and 4. FIGS. 2 to 4 also show a component of one instrument which can be used with the devices of the present invention.

Referring now to FIG. 1, this preferred device comprises a housing 60 which defines holding chamber 61 and test chamber 63. Housing 60 is provided with flange 67 and tab 69.

The geometry of housing 60 which defines holding chamber 61 and test chamber 63 is selected to minimize the possibility of an air bubble being trapped in the device and in preferred embodiments the bottom of holding chamber 61 is sloped to minimize air entrapment when blood is added through opening 65. The section of housing 60 defining holding chamber 61 is tapered at opening 65 for ease of inserting, e.g., a pipette tip for delivering blood to holding chamber 61.

The geometry of the housing is selected to maximize surface contact of the blood to the heated surface of the housing, while at the same time minimizing the area of blood exposed to the air to minimize risk of sample degradation. In the embodiment shown in the figures, the L-shaped configuration of housing 60 accomplishes both of these objectives.

Test chamber 63 is adapted to receive sample cup 10. Sample cup 10 supports a reagent treated partition member 6 having aperture 9 therein and a capillary hub 30 which provides a mechanism to operably attach transfer member 40 to sample cup 10. The interior of sample cup 10 is provided with four vacuum chuck stop ribs 14 for positioning, two of which are shown in FIG. 1.

Housing 60 is adapted to mate with an instrument which can create a vacuum in test chamber 63 or in a part of test chamber 63. In the embodiment shown, this is accomplished by rim 12 of sample cup 10 which comprises a part of test chamber 63. The instrument has a mating component which is capable of sealably mating with rim 12 of sample cup 10. In the embodiment shown in FIGS. 2 to 4, the mating component comprises vacuum chuck 15 shown. Vacuum chuck 15 is provided with O-ring 27 which during the assay sealably meets rim 12. The contact is sufficient to enable vacuum chuck 15 to create a vacuum in sample cup 10. Vacuum chuck 15 is moved by the instrument to contact rim 12 and to exert a downward pressure on sample cup 10 to move transfer member 40 towards pierceable member 70, causing it to pierce the pierceable member and extend into sample 11 in the holding chamber. Vacuum chuck stop ribs 14 in sample cup 10 limit the downward movement of vacuum chuck 15.

FIG. 2 shows a cross section view of the device shown in FIG. 1 along line 2—2 before vacuum chuck 15 has exerted downward pressure on sample cup 10. FIG. 3 shows a cross section view of the device shown in FIG. 2 after vacuum chuck 15 has moved to contact and move sample cup 10 downward so that the bottom of sample cup 10 is in contact with support member 71 and a transfer member, in this embodiment capillary 40 has pierced pierceable member 70 and penetrated into sample 11. As shown in FIG. 3, support member 71 contacts the bottom of sample cup 10 under the downward pressure of the instrument.

The instrument is then able to create a vacuum in test chamber 63, e.g., by the movement of a syringe pump. This vacuum or negative pressure causes sample 11 to flow from holding chamber 61 through capillary transfer member 40 into receiving chamber 18 and through aperture 11 in partition member 6 as shown in FIG. 4. In the case of test cartridges for use in the vWf deficiency assay, reagents on partition member 6 activate the formation of a platelet plug which eventually occludes aperture 9 and the flow of sample through transfer member 40 ceases. The time required for the blood flow to cease, termed "closure time," is then compared with the time required for blood flow to cease when the platelet function of the blood is normal. A normal range within which blood flow should stop is obtained by testing normal blood.

Opening 9 in partition member 6 is dimensioned so that under the conditions of the particular assay a plug will be formed and the opening closed. If the aperture is too small non-assay related blockages will occur. If it is too big then a plug will not form properly. For the platelet function test, the aperture is preferably between about 100 microns to about 200 microns, more preferably about 140 microns to 160 microns, most preferably about 150 microns. The dimension of the aperture in partition member 6 does not have a great influence on the initial flow characteristics in the device.

Receiving chamber 18 shown in FIGS. 2 and 3 is positioned in test chamber 63 between partition member 6 and capillary hub 30. Receiving chamber 18 is dimensioned so that blood entering from capillary 40 does not enter too close to the membrane and disturb the forming plug.

Partition member 6 is a porous or non-porous support matrix for one or more agents capable of initiating platelet aggregation in anticoagulated whole blood and platelet-rich plasma. For example, in a device specifically adapted for testing platelet function, the blood entry side of the partition member comprises a collagen material as disclosed in U.S. Pat. No. 4,604,894 and 5,051,239. When platelets in the aspirated and anticoagulated blood come in contact with collagen on the porous member, activation and aggregation events take place around the aperture, ultimately forming a platelet plug which occludes the aperture and causes cessation of blood flow. The preferred material for the partition member has absorbency to liquids so that reagents can be applied yet has a stable structure so that a precise opening can be, for example, punched.

Preferred porous partition members for use in the test cartridge and methods of the present invention include cellulose esters, ceramic, nylon, polypropylene, polyvinylidene fluoride (PVDF), and fiberglass. A particularly preferred porous partition member is a mixed cellulose ester (acetate and nitrate) membrane from Millipore.

In embodiments wherein the partition member is provided with a collagen coating, a uniform layer of collagen around the aperture is highly desirable. The amount of collagen on the membrane is not particularly critical. A range of about 1–2 $\mu$g has been found to perform well in the platelet function assay. In one test cartridge of the present invention, collagen is provided to the porous partition member and then the porous partition member is dried for storage in the housing under a hermetic seal.

The present invention also provides porous partition members having incorporated therein standard platelet aggregation modulating agents, such as epinephrine or adenosine 5'-diphosphate (ADP). In one preferred test cartridge of the present invention, lyophilized epinephrine bitartrate (about 10 μg) was incorporated in a porous partition member.

These agents provide controlled stimulation to the platelets as the blood sample passes through the aperture. The collagen surface serves as a matrix for platelet deposition and attachment.

The aperture closure time with a normal blood sample depends in part upon the concentration of the biologically active substance incorporated in the membrane. The concentration of agents is selected so as to provide a convenient distinction between normal and abnormal coagulation parameter. This can be readily determined by one of ordinary skill in the art. The concentration ranges of similar reagents reported for use in aggregometry provide one starting point in determining the appropriate concentration range. Reagent concentrations are optimized keeping in mind the desired sensitivity of the assay. For example, it is desirable that the concentration of epinephrine be sufficient to detect mild platelet dysfunction, but not so low as to introduce variable results.

A threshold amount of epinephrine is needed for complete activation and aggregation and if mild platelet dysfunction is being studied, then a smaller amount of reagent is used. It can be seen that a balance between the sensitivity of the test and obtaining reproducible results is desired. The sensitivity of the test can be controlled by altering the amount of epinephrine bitartrate incorporated into the porous partition member. For example, when less epinephrine is used, e.g., about 5 μg, the assay is more sensitive than when about 20 μg is used. One skilled in the art can easily determine the amount of epinephrine to use based upon the desired sensitivity of the assay. The ranges of closure times for normal blood will be different depending on the amount of epinephrine used in the porous partition member. One skilled in the art can readily determine the standard ranges of closure times for the amount of epinephrine selected. In preferred embodiments, about 10 μg epinephrine bitartrate is incorporated into the membrane.

As shown in FIGS. 2 and 3, test chamber 63 is provided with a two position support for sample cup 10, the support comprising support member 71 and crush rib 72. Support member 71 has a central opening dimensioned to permit section 31 of capillary hub 30 to pass therethrough. As shown in FIG. 2, crush rib 72 (others not shown) maintain sample cup 10 in a first position so that capillary 40 is above but not in contact with pierceable member 70. As shown in FIG. 3, sample cup 10 has been moved into a second position whereby crush ribs 72 have been compressed, sample cup 10 is in contact with and held in position by support member 71, section 31 of capillary hub 30 has passed through support member 71, and capillary 40 has been moved towards and through pierceable member 70 to project into holding chamber 61 and into sample 11 disposed therein.

Sample is caused to flow from holding chamber 61 to test chamber 63 by the vacuum created by the instrument.

The initial rate of flow through the device is controlled by varying the length and the inner diameter of the capillary.

In platelet function tests, for a sample volume of about 500 to 800 μl it is preferred that the initial flow rate of blood through the device be from about 100 μl to about 200 μl per minute. It is believed that diameters much less than 100 micron will have an effect on platelets. Accordingly, the preferred inner diameter of capillary 40 is from about 100 to 220 microns. A particularly preferred inner diameter is about 150–210μ and a preferred length of the capillary is about 0.6–1.2 inches long. In an especially preferred embodiment the inner diameter of the capillary is about 200±10 microns and the length of the capillary is about 1.2 inches. With this configuration and flow, the aperture in the membrane will close in about 1 to 3 minutes if the blood has normal platelet function.

When using the collagen/epinephrine test cartridge with normal blood, closure times ranging from about 98–185 seconds are observed. See Mammen, E. F., et al., *Seminars in Thrombosis and Hemostasis*—Volume 21, Suppl. 2, pp. 113–121, 1995. When blood from patients with a platelet dysfunction (as judged by conventional testing and clinical indications) is used, closure times greater than the normal range (e.g., greater than about 185 seconds) are obtained using the collagen/epinephrine test cartridge. Therefore, a closure time which exceeds values within the normal range for the particular device used to carry out the assay indicate platelet dysfunction. This test, like others in the art for measuring platelet function, does not however discriminate among the many deficiencies that can cause the platelet dysfunction. To do so requires additional testing which, by currently known methods, is time consuming and complicated.

Once it is determined that the patient's blood exhibits platelet dysfunction, the assay of the present invention indicates the deficiency of vWf as the cause of the platelet dysfunction by adding a preparation containing vWf to a sample of the patient's whole blood and retesting the sample for platelet function. A normal closure time indicates a correction in the vWf level in the patient's blood and this indicates the presence of vWf deficiency in the patient.

This assay is useful in indicating vWf deficiency, e.g., an abnormal amount of vWf, a substantial absence of vWf or a lack of functional vWf protein. An example of vWf deficiency where the vWf deficiency is due to an abnormal amount of the vWf protein comprises Type I vWD. A substantial absence of vWf protein occurs when the sample contains an amount of vWf significantly lower than the amount necessary for normal hemostasis, such as in Type III vWD. Finally, certain types of von Willebrand disease result from the lack of functional vWf protein, such as in Type IIA and IIB vWD. In Type IIA, the vWf lacks the intermediate and high molecular weight multimers. The method of the present invention is especially useful for indicating a vWf deficiency due to the lack of functional vWf protein of the Type IIA variety. In Type IIB vWD, the vWf lacks the high molecular weight multimers and the vWf has an increased affinity for the platelet receptor glycoprotein Ib (GPIb). Therefore the platelets tend to be saturated with vWf. The saturation of platelets with vWf which occurs in Type IIB affected patients may impact the efficacy of the assay. If inconclusive results are obtained and Type IIB vWD is suspected, additional testing by other methods may be required. One example of such a method is the addition of low dose amounts of ristocetin to another aliquot of the patient's blood sample. If Type IIB vWD is present, aggregation of platelets will be observed, e.g., in an aggregometer.

The blood sample for use in the method of the present invention is prepared the same way as that used to initially test platelet function, i.e., it is treated with an anticoagulant. Any anticoagulant known in the art can be used in this method (e.g., sodium citrate, heparin, hirudin). However, it is preferred that the anticoagulant not remove excessive amounts of calcium (e.g., EDTA) or otherwise interfere with platelet aggregation.

Any preparation known in the art containing vWf is useful in the assay. In one preferred embodiment, the vWf preparation comprises purified vWf. In another preferred embodiment, the preparation comprises platelet-poor plasma containing normal levels of vWf.

vWf is present in is natural form as a multimeric glycoprotein. While the inventors do not intend to be limited by theory, it is hypothesized that the processing involved in currently available commercial preparations of purified vWf alter the composition of the vWf, perhaps by disrupting its multimeric composition, resulting in a preparation which is different, or less active, than that found in normal human plasma. Thus, the amount of purified vWf for use in this assay must be optimized to obtain an activity comparable to the activity of vWf in normal blood. Such activity and its optimization are readily accomplished by one of skill in the art. Purified vWf useful in carrying out the assay of the present invention may be from a human or animal (e.g., bovine) source and obtained from sources known in the art (e.g., purified vWf from American Diagnostica).

Preferably the purified vWf is added in an amount within the range of from about 3 $\mu$g/mL to about 100 $\mu$g/mL, more preferably from about 10 $\mu$g/mL to about 80 $\mu$g/mL, most preferably 30 $\mu$g/mL to 50 $\mu$g/mL. When using commercially available preparations of purified vWf (e.g., American Diagnostica), it is preferred that the factor be added at a concentration higher than the vWf concentration in normal plasma which is approximately 3–12 $\mu$g/mL.

Other sources of vWf are available, such as factor VIII concentrate, which contains levels of vWf comparable to normal blood and is used as a therapeutic in hemophilia and in von Willebrand disease. As discussed above, preferably the amount of factor VIII concentrate used is that required to obtain an activity (i.e., platelet adhesion and aggregation) comparable to the activity of normal blood. This amount can be determined and optimized for a particular batch of factor VIII by one of ordinary skill in the art.

Recombinant vWf would also provide a source of highly active and pure vWf for use in the present invention.

In another preferred embodiment, the vWf preparation useful in carrying out the present assay comprises platelet-poor plasma containing a normal level of vWf (e.g., 3–12 $\mu$g/mL). In this embodiment, the assay further comprises separating the whole blood sample which exhibits platelet dysfunction into a plasma layer and a cellular component layer, removing the plasma layer, and adding the vWf preparation to the cellular layer of the sample. The vWf preparation comprises fresh normal pooled platelet-poor plasma or freshly-thawed frozen normal pooled platelet-poor plasma containing normal levels of vWf. The plasma can be either human or animal (e.g., bovine) plasma and can be provided by a donor or as commercially available frozen plasma. Preferably a volume of this plasma, equal to the volume of the removed plasma, is added and the sample gently mixed, as is known in the art, to ensure thorough mixing of the plasma and cells and homogeneity of the sample. The resulting mixture is a reconstituted blood sample.

The blood sample mixed with a vWf preparation as taught herein is then tested for platelet function. In one preferred embodiment of the present invention the testing of platelet function comprises measuring closure time in a device for testing coagulation function of blood. Preferably this testing is done in a PFA-100™ test cartridge as described above and shown in FIGS. 1–4, and most preferably with a collagen/epinephrine test cartridge. The results of the testing prior to addition of the factor preparation are compared with the results subsequent to the addition. If addition of a vWf preparation as taught herein produces normal platelet function in the sample, this strongly suggests that the previously seen abnormal function was due to vWf deficiency. For example, when using the test cartridge described above, if a correction in the closure time is observed, i.e., the closure time is in the normal range, there is a strong indication that the abnormal closure time initially observed in the blood sample was due to vWf deficiency in the sample. The clinician may then decide to perform additional tests on the patient to confirm the diagnosis of vWf deficiency.

While the PFA-100™ is a preferred device, the method of this invention is not limited by the device for testing platelet function of blood. The method is useful in conventional aggregometers and other tests devices known in the art. For example, the method can be used in the in vitro test system described by Brubaker by performing measurement prior to and after addition of the purified vWf to the sample. If a correction in the time required for the cessation of blood flow is observed, vWf deficiency in the sample is indicated. A similar approach could also be utilized with the Xylum CSA analyzer (Xylum Corp., NY) and O'Brien filter bleeding time techniques. O'Brien, J. R., *Thromb.Res.*, 76:103–108 (1994).

In some of the test devices, such as conventional aggregometers, it is preferable to perform the tests on platelet-rich plasma (PRP), rather than blood. The PRP is obtained by methods known in the art, e.g., centrifugation. In this embodiment, the PRP is run in the test device, with an appropriate agonist to stimulate platelet aggregation. The absence of aggregation may indicate vWf deficiency as the cause. To confirm vWf deficiency, a vWf preparation as described above, is added to another PRP sample from the patient and the sample is run through the test device. If aggregation is observed, vWf deficiency is indicated. The vWf preparation useful with PRP is preferably purified von Willebrand factor or platelet-poor plasma containing a normal level of vWf, as described above.

Once platelet dysfunction is identified, the method of the present invention enables the rapid identification of vWf deficiency. When blood samples are tested according to methods of the present invention and using the PFA-100™ device, the test can be performed within approximately 30 minutes in contrast to prior art tests which require at least 8–16 hours. Preferably, results are obtained within 10 minutes when using the PFA-100™ system. This rapid turnaround obviates the delay seen in prior art vWf tests. When using other types of devices, such as conventional aggregometers, the assay can also be completed within 30 min. This test is therefore useful not only for routine screening for vWf deficiency, but also for applications where determination of platelet function must be obtained quickly, such as emergency room situations.

Another aspect of this invention is a kit for indicating vWf deficiency in a blood sample which exhibits abnormal platelet function comprising a vWf preparation useful in carrying out the method of the present invention, wherein the preparation is added to the sample prior to testing for platelet function. In one preferred embodiment, the kit provides a premeasured quantity of vWf preparation of lyophilized purified von Willebrand factor in a sterilized container or vial. The preparation is preferably supplied in a dry state. In carrying out the assays of the present invention, this preparation is mixed with an amount of sample, whole blood or platelet-rich plasma, for example, 1 mL, so that the sample dissolves the preparation. The mixture is then run in the coagulation testing device to determine the presence or absence of the vWf deficiency, as described above.

The vWf preparation in the kit is stabilized as is known in the art, for example, by adding buffer salts, glycine or sodium chloride buffer and antimicrobial agents. The quantity of purified von Willebrand factor will depend on the quality of the purified factor and can readily be achieved by one of skill in the art. Preferably, the amount of the factor used will provide the equivalent of at least 10 μg vWf per 1 mL of sample. The kit provides enough preparation to run duplicate samples.

In another embodiment of a kit of the present invention, the kit supplies a vial of vWf preparation which comprises normal human plasma with normal levels of von Willebrand factor. In use, a blood sample to be tested is centrifuged to separate the plasma and cellular layers. The plasma layer is removed and an equal volume of the vWf preparation provided by the kit (thawed, if necessary) is added to the sample. The reconstituted sample is then run on the desired test device to determine the presence or absence of vWf deficiency. The amount of plasma provided in the kit is enough to run duplicate samples. A preferred kit provides up to about 2 mLs of plasma, allowing up to 1 mL per sample.

The following examples are provided to more clearly illustrate the aspects of the invention and are not intended to limit the scope of the invention.

EXAMPLES

I. Determination of platelet dysfunction

A whole blood sample was collected in 3.8% sodium citrate anticoagulant (1 part anticoagulant to 9 parts blood). The platelet function of the sample was tested using the PFA-100™ test described above, run with collagen/epinephrine test cartridges. Approximately 0.8 mL of sample was used for each PFA-100™ test run, and the test was performed in duplicate. The time required for closure, i.e., cessation of blood flow, was observed. If the closure time was above the normal reference range for the test, then the results indicated platelet dysfunction. If after evaluation of the patient history and the record of medication usage, the clinician suspected von Willebrand disease, then the sample was further tested according to the methods of the present invention as follows.

II. Determination of vWf deficiency—Addition of Plasma

A blood sample from the patient was centrifuged at 1500×g or higher to separate the cellular components from the plasma. The blood sample used in this assay can be taken from the same sample tube as the blood used in part (a) above, i.e., it was mixed with an anticoagulant, e.g., sodium citrate. A 0.8 mL sample was used for each PFA-100™ test run, and the test was performed in duplicate. The platelet-poor plasma collected on top of the layer of cellular components in the centrifuge tube was removed by methods known in the art, such as by aspiration with a pipette. This step was performed carefully to not disturb the cellular layer. The volume of the plasma removed was measured. Preferably at least 85–90% of the plasma collected on top was removed. A volume, equal to that of the removed plasma, of either fresh pooled platelet-poor plasma containing normal levels of vWf, or freshly-thawed frozen normal pooled platelet-poor plasma (George King Biomedical, Overland Park, Kans.) was then added to the centrifuged blood sample. The tube was inverted gently, at least ten times, in order to ensure proper mixing of the plasma and cells and homogeneity of the sample.

The PFA-100™ test was run with the reconstituted blood sample using collagen/epinephrine test cartridges as described in part (a). The time required for closure, i.e., the cessation of blood flow, was observed.

Table 1 shows that 100% substitution of sample plasma with frozen normal pooled plasma results in closure times similar to closure times of normal blood, the control measurement. These results indicate that frozen normal pooled plasma contains an appropriate amount of vWf to obtain closure times comparable to that of normal blood.

TABLE 1

|  | PFA-100 Mean Closure Time, Sec | Comments |
| --- | --- | --- |
| Control measurement | 106 (n = 3) |  |
| 100% plasma substitution with frozen normal pooled plasma (George King Biomedical) | 132 (n = 3) | Off-the-shelf frozen normal pooled plasma has enough normal vWf |
| Control measurement | 171 (n = 2) |  |
| 100% plasma substitution with frozen normal pooled plasma (George King Biomedical) | 161 (n = 2) | Off-the-shelf frozen normal pooled plasma has enough normal vWf |

Table 2 shows that samples of blood from patients suffering from type IIA vWD did not obtain closure of the aperture, i.e., the samples had a mean closure time greater than 300 seconds. There was no closure due to the lack of normal vWf. However, when the plasma of samples of that blood was replaced with an equal volume of fresh normal plasma, the samples had a mean closure time close to that of normal blood. These results indicate that the vWf present in the fresh normal plasma was able to correct the vWf deficiency and produce closure times comparable to those of normal blood.

TABLE 2

|  | PFA-100 Mean Closure Time, Sec | Comments |
| --- | --- | --- |
| Blood sample from vWD[1] type IIA patient | >300 (n = 2) | No closure due to lack of normal vWf |
| Patient plasma replaced with equivolume fresh normal plasma | 151 (n = 2) | vWf from fresh normal plasma was able to correct the defect |

[1]"vWD" indicates von Willebrand disease.

Table 3 shows that when approximately all the plasma of normal blood is replaced with an equal volume of plasma from a patient suffering from vWf type IIA, no closure is obtained. When decreasing amounts of the normal plasma are replaced, the closure times approach that of normal plasma, indicating near normal levels of vWf.

TABLE 3

| | PFA-100 Mean Closure Time, Sec | Comments |
|---|---|---|
| Control whole blood | 116 (n = 1) | Normal closure |
| 750 μL normal plasma replaced with 750 μL vWD type IIA patient plasma | >300 (n = 3) | No closure obtained. Lack of normal vWf due to substitution with patient plasma |
| 500 μL normal plasma replaced with 500 μL vWD type IIA patient plasma | 210 (n = 2) | Prolonged closure indicating reduced level of normal vWf |
| 250 μL normal plasma replaced with 250 μL vWD type IIA patient plasma | 141 (n = 2) | Close to the control value indicating close to normal level of vWf |

III. Determination of vWf deficiency using purified vWf preparation:

In another embodiment of the method of this invention, 40 μg of purified human vWf (American Diagnostica, Inc., Greenwich, Conn.) was added to approximately 1 mL of whole blood sample to obtain a final concentration of factor of 40 μg/mL. The blood sample was carefully mixed by gentle inversion of the tube, approximately 5 times to ensure proper mixing and homogeneity of the sample.

PFA-100™ measurements were then performed using the collagen/epinephrine test cartridges as above. The time required for closure, i.e., the cessation of blood flow, was observed. The results are shown in Table 4. The addition of 40 μg purified vWf per mL of blood resulted in normal closure times.

TABLE 4

| | PFA-100 Closure Time, Sec | Coments |
|---|---|---|
| Blood sample from vWD type IIA patient | >300 (n = 1) | No closure due to lack of normal vWf |
| Purified vWf (American Diagnostica) added at 2.5 μg/mL blood to the blood sample from type IIA vWD patient | >300 (n = 1) | No correction |
| Purified vWf (American Diagnostica) added at 5 μg/mL blood to the blood sample from type IIA vWD patient | >300 (n = 1) | No correction |
| Purified vWf (American Diagnostica) added at 10 μg/mL blood to the blood sample from type IIA vWD patient | 312 (n = 1) | Prolonged closure obtained indicating partial correction |
| Purified vWf (American Diagnostica) added at 20 μg/mL blood to the blood sample from type IIA vWD patient | 307 (n = 1) | Prolonged closure obtained indicating partial correction |
| Purified vWf (American Diagnostica) added at 40 μg/mL blood to the blood sample from type IIA vWD patient | 174 (n = 1) | Closure time is in the normal range. Correction occurred due to addition of high conc. of purified vWf |

As demonstrated in the Examples, a closure time observed after addition of a suitable vWf preparation in the normal range provides a strong indication that the abnormal closure time observed initially was due to vWf deficiency in the sample. The clinician may then decide to confirm the diagnosis of vWf deficiency using other tests.

IV. Determination of vWf deficiency using Aggregometry.

A blood sample obtained from a patient is centrifuged at 150×g to obtain platelet-rich plasma (PRP). The PRP is aspirated and separated from the packed red blood cells, by methods known in the art. The blood sample is then centrifuged at 1500×g to obtain platelet-poor plasma (PPP). Platelet count is performed on the PRP. The platelet count of the PRP is adjusted to 150,000/μL by mixing appropriate proportions of PRP and PPP.

An aliquot of the resultant platelet count-adjusted PRP is then analyzed on a standard aggregometer (Chrono-Log Corp., Havertown, Pa.; other devices available from Helena Laboratory, Beaumont, Tex.) using a standard set of agonists (e.g., collagen, ADP, arachidonic acid, ristocetin).

A low platelet aggregation response when using the ristocetin agonist may indicate von Willebrand factor (vWf) deficiency.

Purified vWf is added to another aliquot of the PRP sample, to obtain the equivalent of 40 μg of vWf per mL of sample, and the aggregometry is repeated with ristocetin agonist. If a normal aggregation response is observed, the possibility of vWf deficiency in the original sample is confirmed. The clinician may send the patient for further work-up and confirmation of the disease.

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

What is claimed is:

1. A method for indicating von Willebrand factor deficiency in a blood sample or platelet-rich plasma sample which exhibits abnormal platelet function comprising
   a) adding a von Willebrand factor preparation to the sample under conditions to provide a solution of von Willebrand factor in the sample, and
   b) testing the sample for platelet function by measuring closure time in a device for testing hemostatic function of blood, wherein the von Willebrand factor preparation restores normal platelet function.

2. The method according to claim 1, wherein the von Willebrand factor preparation comprises purified von Willebrand factor.

3. The method according to claim 2, wherein the purified von Willebrand factor is added in amount to obtain an activity comparable to the activity of von Willebrand factor in normal blood.

4. The method according to claim 1 which further comprises
   a) separating the blood sample into a plasma layer and cellular component layer and
   b) removing the plasma layer, prior to the step of adding a von Willebrand factor preparation to the cellular component layer of the sample.

5. The method according to claim 4, wherein the von Willebrand factor preparation comprises platelet-poor plasma containing a normal level of von Willebrand factor.

6. The method according to claim 5, wherein the von Willebrand factor preparation comprises fresh pooled platelet-poor plasma containing normal levels of von Willebrand factor, or freshly-thawed frozen normal pooled platelet-poor plasma.

7. The method according to claim 1 wherein the testing of platelet function comprises measuring closure time in a test cartridge.

8. The method according to claim 1, wherein the von Willebrand factor deficiency comprises an abnormal amount of the vWf protein, a substantial absence of the vWf protein, or a lack of a functional vWf protein.

9. The method according to claim 8, wherein the lack of a functional vWf protein is due to an abnormality in the molecular composition of the vWf protein.

10. The method according to claim 9, wherein the abnormality in the molecular composition of the vWf protein causes type IIA von Willebrand disease.

11. The method according to claim 8, wherein the abnormal amount of vWf protein causes Type I von Willebrand disease.

12. The method according to claim 8, wherein the substantial absence of the vWf protein causes Type III von Willebrand disease.

13. A method for indicating von Willebrand factor deficiency in a blood sample or platelet-rich plasma sample which exhibits abnormal platelet function comprising
   a) separating the blood sample into a plasma layer and cellular component layer;
   b) removing the plasma layer;
   c) adding a von Willebrand factor preparation to the cellular component layer of the sample; and
   d) testing the sample for platelet function by measuring closure time in a device for testing hemostatic function of blood; wherein the von Willebrand factor preparation restores normal platelet function.

14. The method according to claim 13, wherein the von Willebrand factor preparation comprises platelet-poor plasma containing a normal level of von Willebrand factor.

15. The method according to claim 13, wherein the von Willebrand factor preparation comprises fresh pooled platelet-poor plasma containing normal levels of von Willebrand factor, or freshly-thawed frozen normal pooled platelet-poor plasma.

16. The method according to claim 13 wherein the testing of platelet function comprises measuring closure time in a test cartridge.

* * * * *